(12) United States Patent
Fordinal

(10) Patent No.: US 10,543,330 B2
(45) Date of Patent: Jan. 28, 2020

(54) ORAL APPLIANCE AND METHOD OF USE THEROF

(71) Applicant: COOK MEDICAL TECHNOLOGIES LLC, Bloomington, IN (US)

(72) Inventor: Amie L. Fordinal, Houston, TX (US)

(73) Assignee: Cook Medical Technologies LLC, Bloomington, IN (US)

( * ) Notice: Subject to any disclaimer, the term of this patent is extended or adjusted under 35 U.S.C. 154(b) by 304 days.

(21) Appl. No.: 14/596,840

(22) Filed: Jan. 14, 2015

(65) Prior Publication Data

US 2015/0250967 A1  Sep. 10, 2015

Related U.S. Application Data

(60) Provisional application No. 61/948,195, filed on Mar. 5, 2014.

(51) Int. Cl.
*A61M 16/04* (2006.01)
*A61M 16/20* (2006.01)

(52) U.S. Cl.
CPC .... *A61M 16/0488* (2013.01); *A61M 16/0445* (2014.02); *A61M 16/0495* (2014.02); *A61M 16/208* (2013.01); *A61M 2209/06* (2013.01)

(58) Field of Classification Search
CPC ........... A61M 16/0488–0497; A61M 16/0445; A61M 2209/06
See application file for complete search history.

(56) References Cited

U.S. PATENT DOCUMENTS

| | | | |
|---|---|---|---|
| 2,099,127 A | 12/1936 | Leech | |
| 3,543,751 A | 12/1970 | Sheffer | |
| 4,231,365 A | 11/1980 | Scarberry | |
| 4,327,720 A | 5/1982 | Bronson et al. | |
| 4,351,330 A | 9/1982 | Scarberry | |
| 4,681,094 A * | 7/1987 | Rolnick | A61B 1/06 600/185 |

(Continued)

FOREIGN PATENT DOCUMENTS

| | | |
|---|---|---|
| JP | 08-322937 | 12/1996 |
| WO | WO95/06492 | 3/1995 |

(Continued)

OTHER PUBLICATIONS

Extended European Search Report for 15157031.4 dated May 29, 2015, 9 pgs.

(Continued)

*Primary Examiner* — Rachel T Sippel
(74) *Attorney, Agent, or Firm* — Brinks Gilson & Lione

(57) ABSTRACT

The present disclosure relates generally to an oral appliance and to methods of using such a device. More particularly, the disclosure relates to a device including an inflatable balloon and a guide assembly. One aspect of the present disclosure provides an oral device including an elongated member extending from a proximal end to a distal end, and an inflatable balloon attached to the elongated member near the distal end, the inflatable balloon having a central lumen. Another aspect provides a method of intubating a patient using an oral appliance as disclosed herein.

20 Claims, 6 Drawing Sheets

(56) References Cited

U.S. PATENT DOCUMENTS

| | | | |
|---|---|---|---|
| 5,507,279 A * | 4/1996 | Fortune | A61M 16/0472 128/200.26 |
| 5,791,341 A | 8/1998 | Bullard | |
| 6,152,136 A | 11/2000 | Pagan | |
| 6,196,224 B1 | 3/2001 | Alfery | |
| 6,251,069 B1 | 6/2001 | Mentzelopoulos et al. | |
| 6,533,761 B2 * | 3/2003 | Bertoch | A61M 16/0488 128/206.29 |
| 8,459,256 B2 | 6/2013 | Roblejo | |
| 2001/0015206 A1 | 8/2001 | Arndt | |
| 2009/0211574 A1 * | 8/2009 | Sniadach | A61M 16/0488 128/200.26 |
| 2012/0234328 A1 | 9/2012 | Bertram | |
| 2013/0019871 A1 | 1/2013 | Nemirovsky | |
| 2013/0098358 A1 * | 4/2013 | Blom | A61M 16/0488 128/200.26 |
| 2015/0101612 A1 * | 4/2015 | Wang | A61M 16/0463 128/207.15 |
| 2015/0165148 A1 * | 6/2015 | Kozlowski | A61M 16/0434 128/200.26 |
| 2015/0173598 A1 * | 6/2015 | Alexander | A61B 1/00154 600/187 |

FOREIGN PATENT DOCUMENTS

| | | |
|---|---|---|
| WO | WO99/38432 | 8/1999 |
| WO | WO01/91838 | 12/2001 |
| WO | WO2013/138861 | 9/2013 |

OTHER PUBLICATIONS

Communication Under 71(3) EPC Intention to Grant for EP Patent Application No. 15 157 031.4 dated Oct. 18, 2017, 27 pgs.

Examination Report for EP Patent Application No. 15 157 031.4 dated Dec. 6, 2016, 6 pgs.

* cited by examiner

ORAL APPLIANCE AND METHOD OF USE THEROF

RELATED APPLICATIONS

The present application claims priority from U.S. Provisional Patent Application Ser. No. 61/948,195 filed Mar. 5, 2014, the contents of which are hereby incorporated by reference in their entirety.

TECHNICAL FIELD

The present disclosure relates generally to an oral appliance. More particularly, the disclosure relates to a device including an inflatable balloon and a guide assembly. In one embodiment, the device is useful for positioning an endotracheal tube in the airway of a patient.

BACKGROUND

Ventilation is a physiologic process which supplies oxygen to the body and removes carbon dioxide, a gaseous waste product. Ventilation is provided by the rhythmic back and forth motion of air in the trachea, caused by the rhythmic contraction and relaxation of the diaphragm. In seriously ill or injured patients unable to breathe adequately on their own, ventilation can be assisted by inserting an endotracheal tube through the oral or nasal cavity of a patient, a process often referred to as endotracheal intubation. An endotracheal tube is a single or double-lumen catheter that is open at both ends. One end extends outside of the patient and is engaged with a mechanical ventilator for supplying a ventilation fluid. The other end extends between the vocal cords and into the trachea of the patient.

Proper placement of the endotracheal tube typically requires the use of a guide instrument, such as a laryngoscope or a video-laryngoscope, to provide a degree of visualization of the internal anatomy of the patient. The laryngoscope may include a curved blade-like structure that is inserted into the pharynx. The blade-like structure elevates the epiglottis to provide a view of the vocal cords and the glottis, and provides a pathway for the end of the endotracheal tube to be manually directed past the vocal cords, and into the trachea. A handle engaged with the blade extends outside the throat to facilitate manipulation by the medical professional. During the intubation procedure, the professional typically grasps the handle of the laryngoscope with one hand, and controls the position of the endotracheal tube with the other hand.

With the patient lying on his or her back, the laryngoscope is typically inserted into the mouth on the right side, and then moved to the left side to move the tongue out of the line of sight. The blade is then lifted in an upward and forward motion to elevate the epiglottis such that the line of sight to the glottis is achieved. During this intubation process, the presence of a second, and sometimes even a third, person is generally required in order to manipulate the patient's head and jaw into alignment to enable optimal visualization of the vocal cords, and to assist with insertion of the endotracheal tube. Since both the laryngoscope and the endotracheal tube must be inserted into a small space in the vicinity of the vocal cords, the intubation procedure typically requires a high degree of experience and care on the part of the intubation team in order to ensure proper visualization and placement of the endotracheal tube, and to avoid damage to the vocal cords and other anatomical structures during the process of inserting the tube. The placement procedure is sometimes further complicated by edema, large tongues, facial trauma, and is particularly difficult in patients with Malenpatti scores of 2-4.

Moreover, devices such as laryngoscopes require a lot of force and often lead to broken teeth, soft palate abrasions, and other complications. Although the video laryngoscope allows the user to visualize the vocal cords after physical manipulation of the epiglottis such devices are expensive.

SUMMARY

In one aspect, the present invention provides a device including an elongated member extending from a proximal end to a distal end, and an inflatable balloon attached to the elongated member near the distal end, the inflatable balloon having a central lumen.

In one embodiment the elongated member includes a concave upper surface forming a channel extending from the proximal end to the distal end. When the balloon is inflated, the central lumen aligns with the channel to form a continuous pathway from the proximal end to the distal end of the oral appliance. In another embodiment, the inflatable balloon assumes a ring shape around the central lumen when in an inflated configuration. In this embodiment, the central lumen aligns with the channel to form a continuous pathway from the proximal end to the distal end of the oral appliance. In one embodiment, the balloon is a toroidal balloon.

In yet another embodiment, the inflatable balloon includes a central region, a first end and a second end. The central region attaches to the elongated member and the first and second ends extend upwards from the upper surface of the elongated member and partially around the central lumen to form a continuous pathway from the proximal end to the distal end of the oral appliance. In another embodiment, the first and second balloon ends attach to the elongated member and the central region of the balloon extends above the upper surface of the elongated member and around the central lumen to form a continuous pathway from the proximal end to the distal end of the oral appliance.

In another embodiment, the device also includes an inflation tube extending from the proximal end of the elongated member to the inflatable balloon and is in fluid communication with the inside of the inflatable balloon. In certain embodiments, the inflatable balloon assumes a lateral dimension of between 1 inch and 3 inches when inflated. In other embodiments, the laterally curved member has a longitudinal dimension of between 2 inches and 6 inches.

Another aspect of the present invention provides a method for displacing tissues within the mouth of a patient, for example, the soft palate or epiglottis. In a preferred embodiment the invention provides a method of intubating a patient. In one embodiment, the method includes inserting the distal end of an oral appliance as disclosed herein into a mouth of the patient and positioning the inflatable balloon at the back of the mouth. The balloon is inflated to a degree sufficient to expose vocal cords of the patient. An intubation tube is positioned on the concave channel of the elongated member and advanced distally along the channel to position the distal end of the intubation tube in the trachea of the patient.

Yet another aspect of the present invention provides a kit including the device as disclosed herein and a syringe or other inflation device. In one embodiment, the device and the inflation device are supplied packaged in a sterile condition. In another embodiment, the kit also includes an inhibition tube.

DETAILED DESCRIPTION OF THE PREFERRED EMBODIMENTS

Definitions

Figure 1:
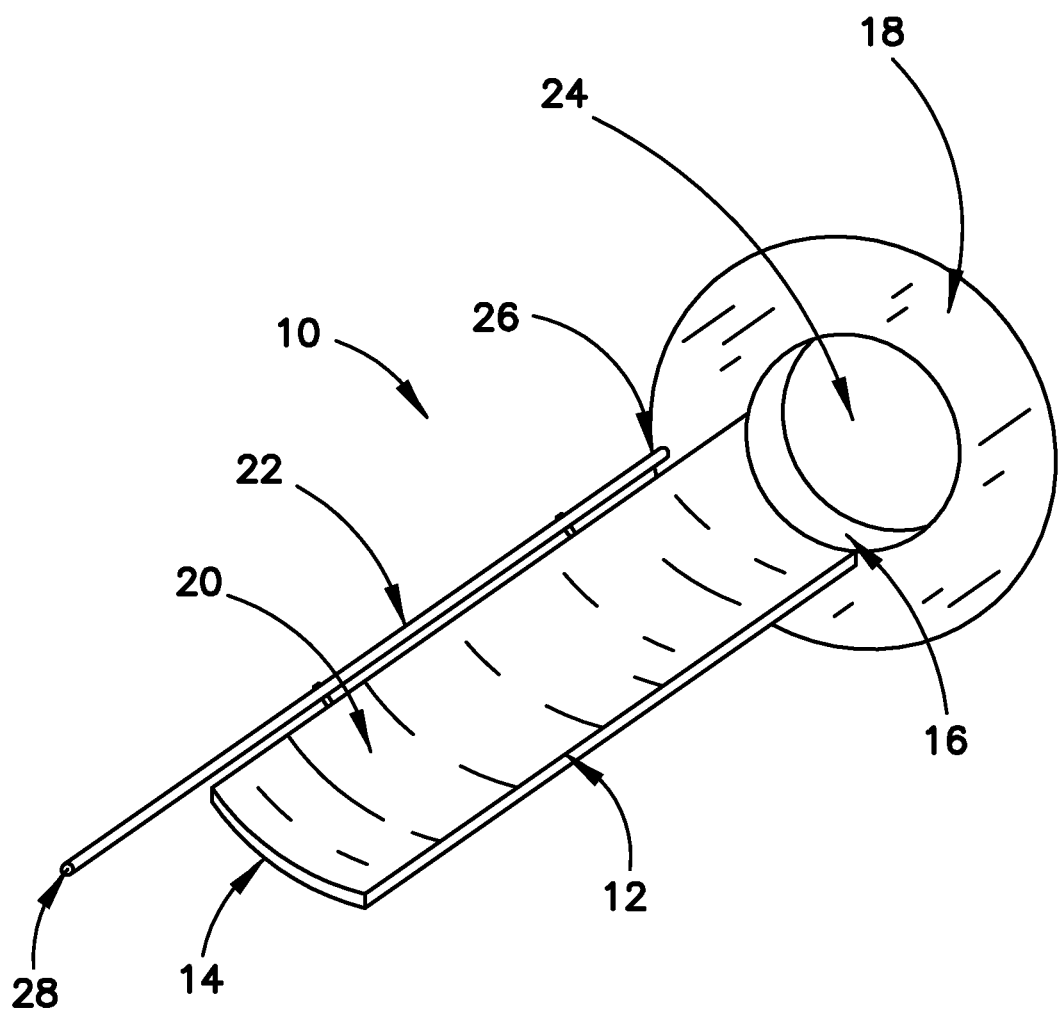
FIG. 1 is an illustration of an oral appliance according to one embodiment of the present invention.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the intubation guide assembly, as well as the axial ends of various component features. The term "proximal" is used in its conventional sense to refer to the end of the assembly (or component) that is closest to the medical professional during use of the assembly. The term "distal" is used in its conventional sense to refer to the end of the assembly (or component) that is initially inserted into the patient, or that is closest to the patient during use. The term "longitudinal" will be used to refer to an axis that aligns with the proximal-distal axis of the oral appliance. The term "lateral" will be used to refer to an axis or plane that is perpendicular to the proximal-distal axis of the oral appliance.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

FIG. 1 is a perspective view of one example of an oral appliance 10. Device 10 includes an elongated member 12 extending from a proximal end 14 to a distal end 16. In the embodiment shown in FIG. 1, elongated member 12 is a laterally curved member having a concave upper surface 20 providing a guide channel extending from proximal end 14 to distal end 16. In other embodiments, upper surface 20 is flat or substantially flat.

Balloon 18 attaches to elongated member 12 at or near distal end 16. In the embodiment shown in FIG. 1, balloon 18 is a ring-shaped balloon and is illustrated in an inflated configuration. Balloon 18 defines a central lumen 24, which aligns with elongated member 12 to form a continuous pathway from proximal end 14 to distal end 16 and through central lumen 24. In one embodiment, balloon 18 is a toroidal balloon.

Inflation tube 22 is in fluid communication with the inside of inflatable balloon 18 and extends from balloon port 26 of inflatable balloon 18 to at least proximal end 14 of elongated member 12 and terminates at inflation port 28. Inflation tube 22 can include a one-way valve or other mechanism (not shown) to maintain balloon 18 in an inflated configuration. Inflation tube 22 may extend along a side of elongated element 12 as illustrated in FIG. 1 or, alternatively, may be placed below, above or incorporated into the structure of elongated element 12.

Figure 2:
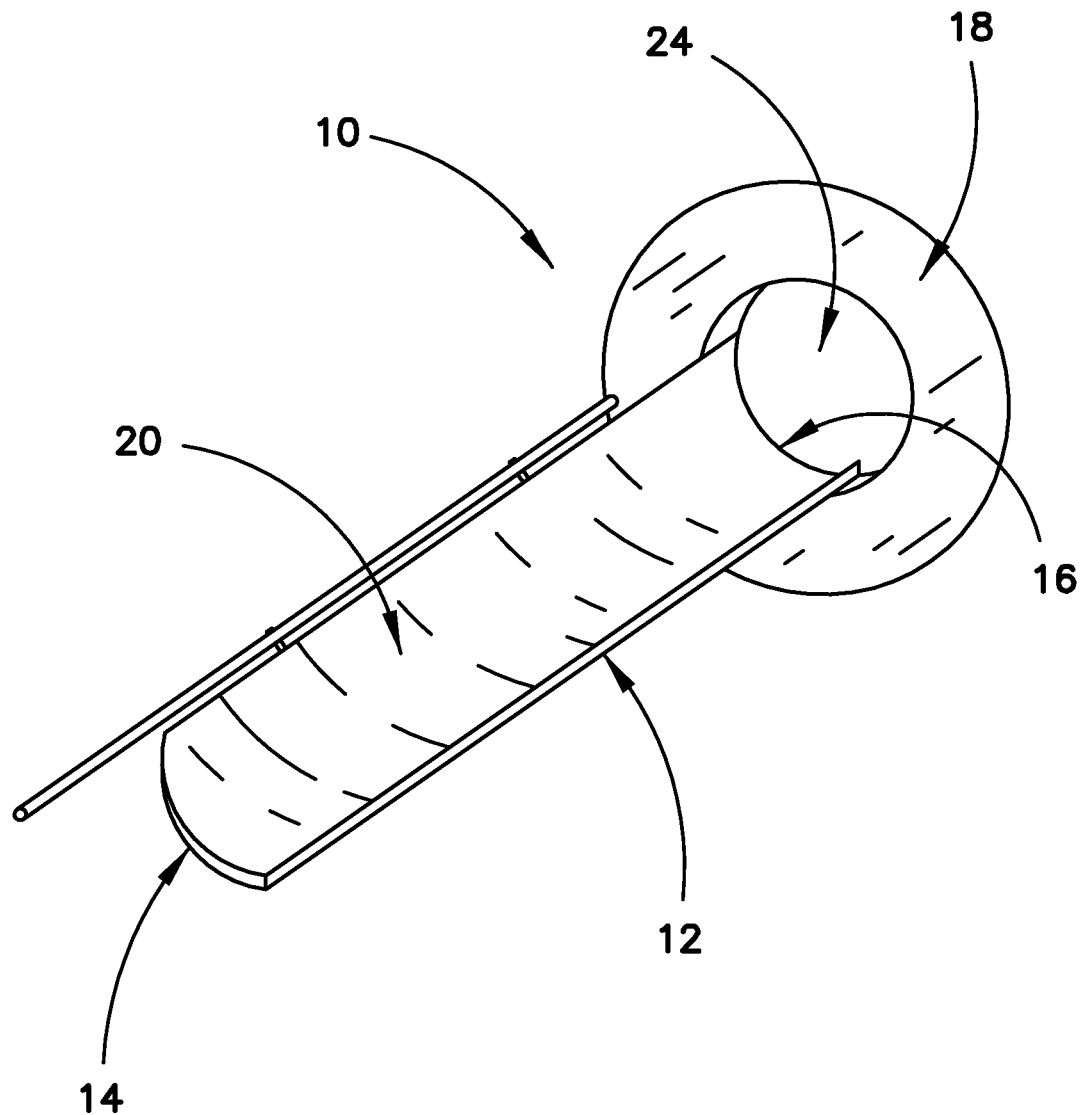
FIG. 2 is an illustration of an oral appliance according to another embodiment of the present invention.
Figure 3:
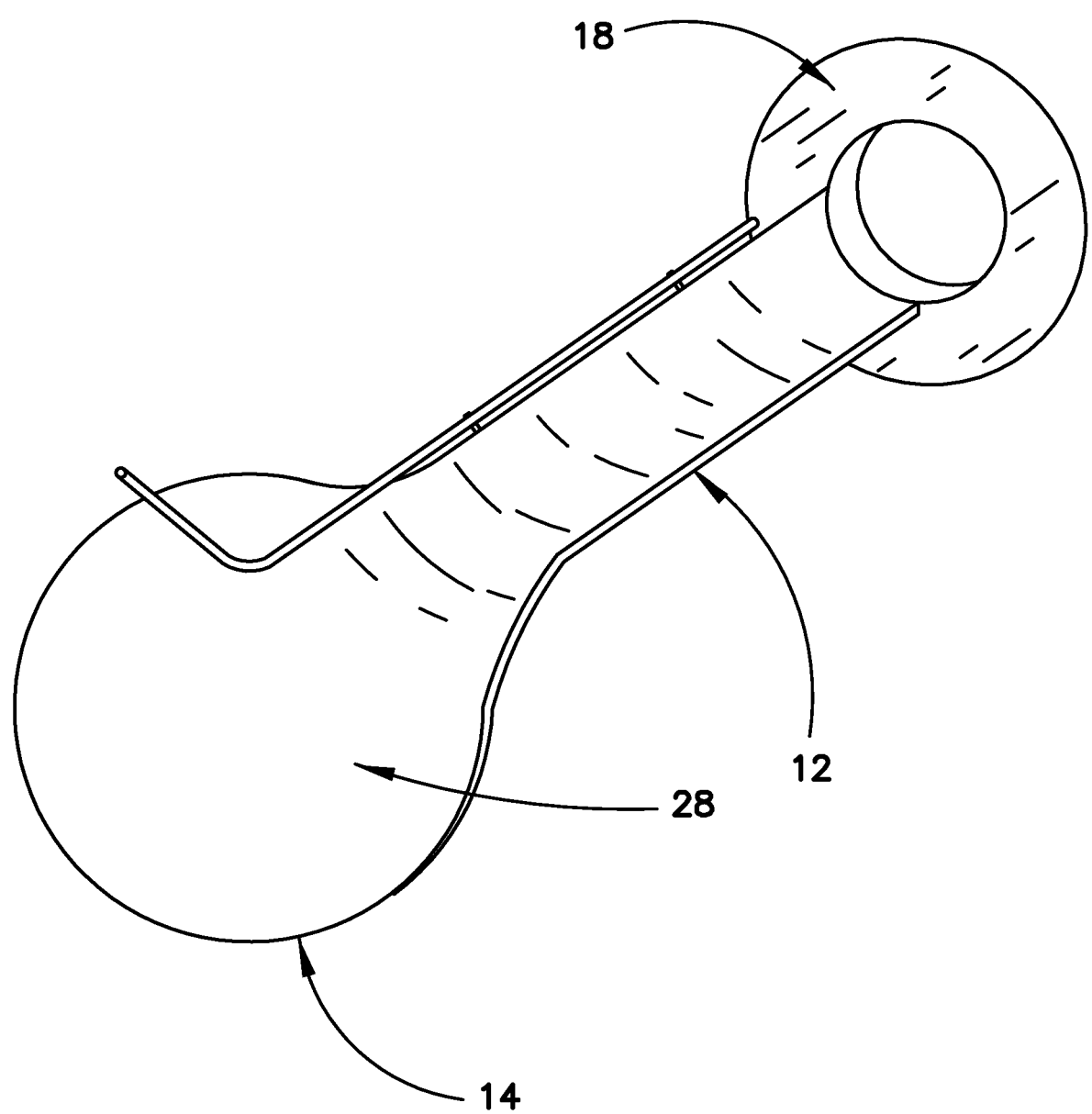
FIG. 3 is an illustration of an oral appliance according to yet another embodiment of the present invention.

FIG. 2 is a perspective view of another example of an oral appliance 10. Here, elongated member 12 includes a more concave upper surface 20 providing a deeper guide channel extending from proximal end 14 to distal end 16 and through lumen 24 of balloon 18. In one embodiment, the guide channel forms a semi-circular channel. FIG. 3 is a perspective view of yet another example of an oral appliance 10. In this embodiment, proximal end 14 of elongated member 12 is expanded to form handle 28. If desired, the grasping surface of handle 28 may be knurled, dimpled, grooved, etc., to enhance grippability.

Figure 4:
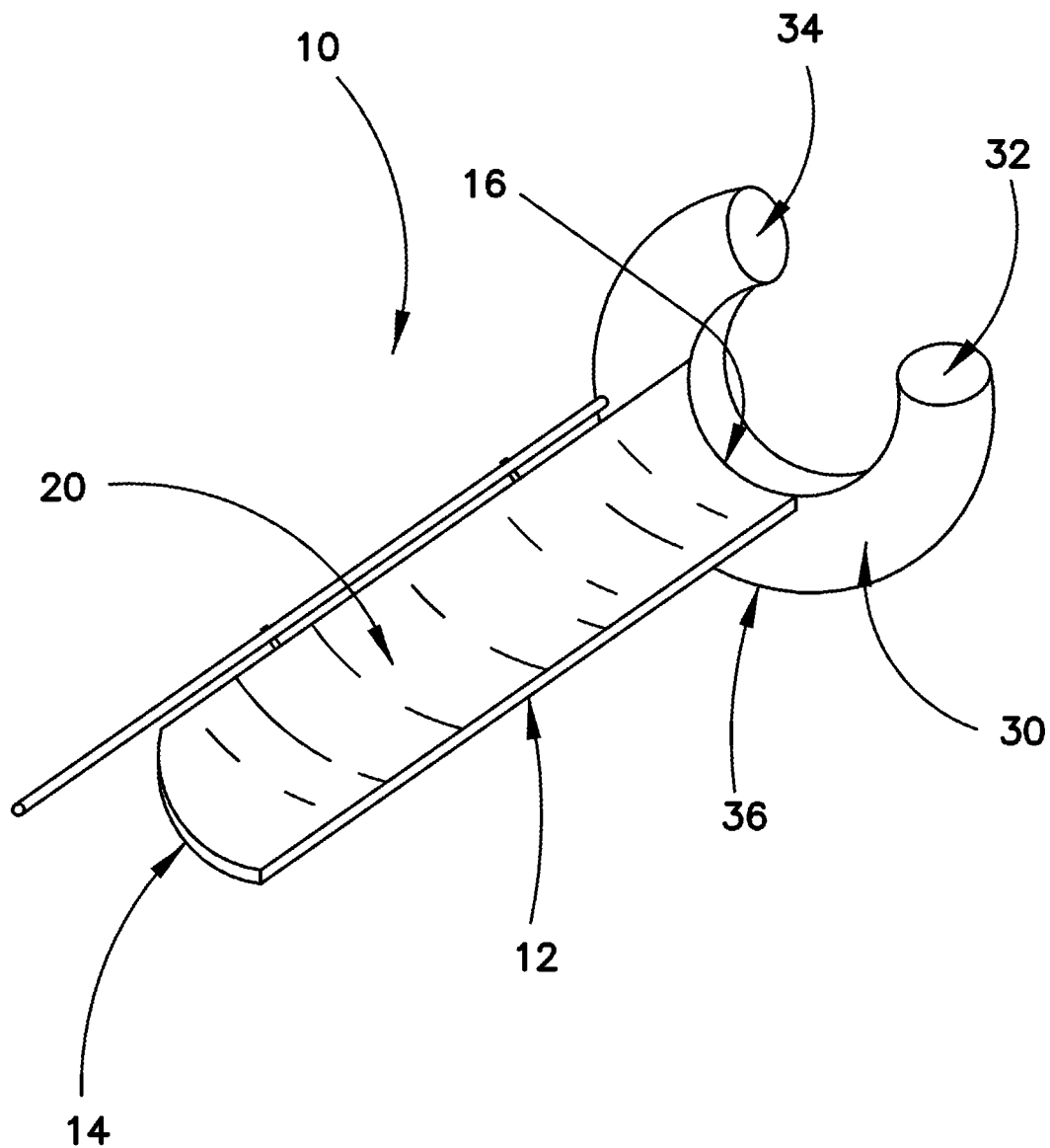
FIG. 4 is an illustration of an oral appliance according to another embodiment of the present invention.

FIG. 4 is a perspective view of an oral appliance 10 including a generally U-shaped balloon 30 having middle portion 36, attached at or near distal end 16 of elongated member 12, and two end segments extending upwards from upper surface 20 of elongated member 12 and terminating at balloon segment ends 32 and 34. Here, balloon 30 is illustrated in an inflated configuration. In certain embodiments, balloon 30 has the shape of an angular segment of a ring or torus. In other embodiments, the balloon has a horse-shoe shaped profile.

Figure 5:
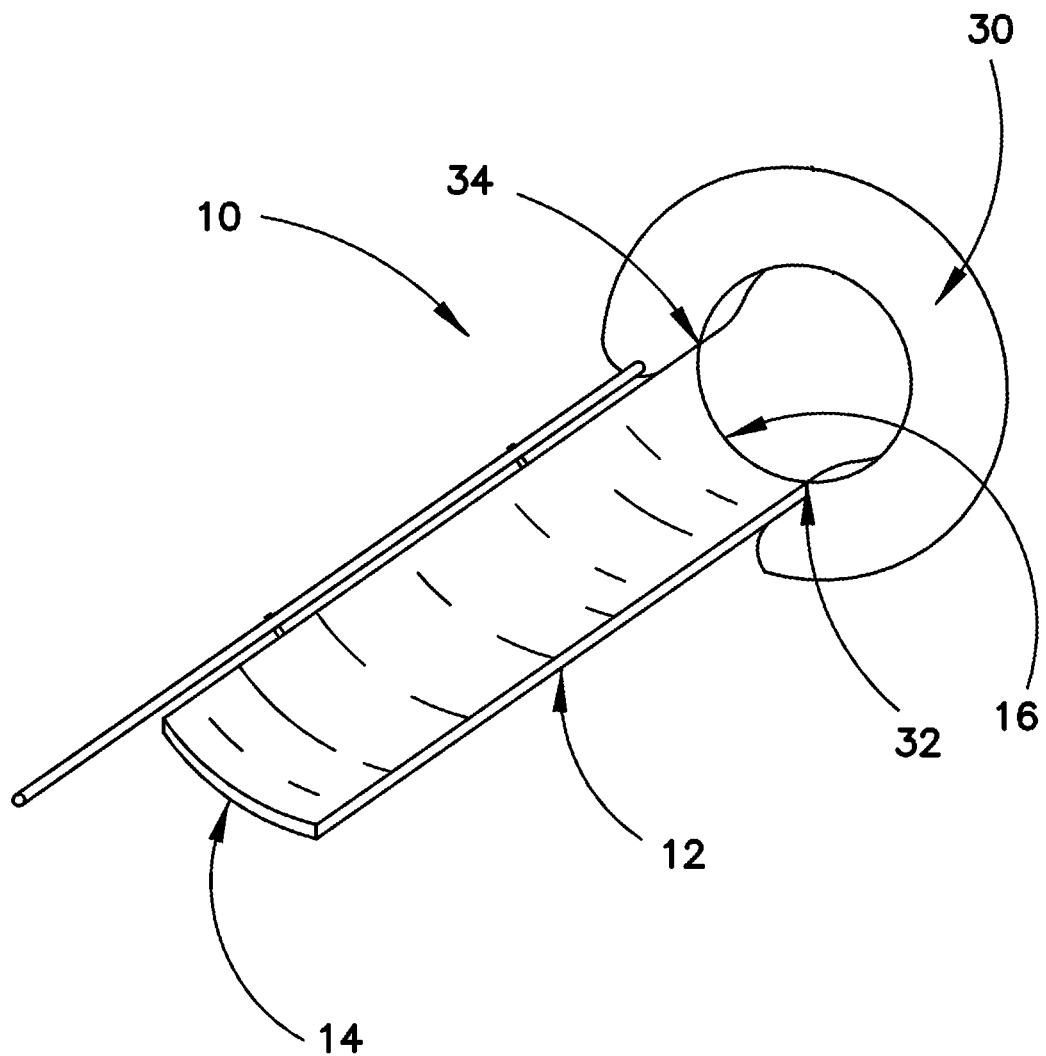
FIG. 5 is an illustration of an oral appliance according to yet another embodiment of the present invention.

FIG. 5 is a perspective view of another embodiment of an oral appliance 10 including a generally U-shaped balloon 30. In this embodiment, balloon 30 is positioned in an inverted U configuration so that balloon segment ends 32 and 34 attach to distal end 16 of elongated member 12. In one embodiment, segment ends 32 and 34 attach to the upper surface of elongated member 12 in a manner such that, when inflated at the back of the mouth of a patient, balloon 30 pushes elongated member 12 downwards against the tongue of the patient.

In certain embodiments, oral appliance 10 is sized and shaped for use with an adult or pediatric human patient. For example, inflatable balloon 10 may assume a lateral dimension of between 0.5 inches and 4 inches, or between 1 inch and 3 inches when inflated. In other embodiments, elongated member 12 may have a longitudinal dimension of between 2 inches and 12 inches, or 3 inches and 10 inches, or 4 inches and 9 inches. Elongated member 12 may be formed from any biocompatible material. For example, this member may be formed from a biocompatible polymer, such as polyethylene, a polyurethane, polyvinyl chloride or silicone; or stainless steel.

The balloon, for example, balloon 18 or balloon 30, may be a compliant balloon or a semi-compliant balloon. In one embodiment, the balloon is manufactured from a silicone.

However, other biocompatible materials can also be used. Such materials include, but are not limited to, biocompatible polymers such as polyethyleneterepthalate (PET), polyvinyl chloride, polypropylene, polyethylene, polyurethanes, nylons, polyesters, latex, natural rubber, synthetic rubber, elastomers and mixtures or copolymers of these materials. The balloon may include a single layer or may be formed from multiple layers of the same or different material. For example, the balloon can contain an inner-most layer of PET, which provides a higher pressure balloon, surrounded by an outer layer of nylon, which provides a surface more resistant to puncture.

In those embodiments where the balloon completely surrounds the central lumen, the balloon may be a circular balloon, for example, the ring-shaped balloon illustrated above. In other embodiments, the balloon may be oval, square or rectangular, or even have an irregular shape around the central lumen. All that is required is that the balloon acts to open up the passageway at the back of the mouth when inflated and provides a central lumen for insertion of a device, for example an intubation tube. A cross-section through the balloon may have a circular, oval, elliptical or other lateral cross section. The cross-section may vary with position around the angular axis of the balloon.

In other embodiments, for example in those embodiments where the balloon extends only partially around the central lumen, the balloon is an elongated balloon having a circular, oval, elliptical or other cross-section. The cross-section of the balloon may vary with position along the axis of the balloon. The elongated balloon is curved along its elongated axis (a curved balloon) such that the ends on the balloon are separated by a distance that is less than the length of the balloon as measured along the curved elongated axis. In one embodiment, the ends of the balloon may touch when the balloon is inflated or may leave only a narrow slit between the ends of the balloon. In some embodiments, a central portion of the elongated balloon is attached at or near the distal end of elongated member 12 in a manner such that the ends of the balloon extend upwards from the upper surface of elongated member 12 to define the central lumen. Such a configuration is illustrated in FIG. 4 with reference to generally U-shaped balloon 30.

In other embodiments, the ends of the elongated balloon attach at or near the distal end of elongated member 12 while the central portion of the balloon extends above the upper surface of elongated member 12 to define the central lumen. Such a configuration is illustrated in FIG. 5 with reference to generally U-shaped balloon 30.

In the embodiments described above, the balloon may attach at the distal end of the elongated member such that it extends distally from the elongated member. In other embodiments, the balloon attaches to the elongated member in a member such that the elongated member extends distally beyond the balloon. For example, in the later embodiments, the elongated member may provide a guide for an intubation tube that extends distally beyond the balloon.

The use of oral appliance 10 during the intubation process will now be described with reference to the device illustrated in FIGS. 1 and 6. However, the principles applied here are also applicable to the use of other embodiments of the oral appliance, such as those disclosed above. Moreover, the use of the appliance is not limited to the intubation process. The appliance may be used to assist in any procedure in which the tissues of the mouth, such as the soft palate, epiglottis or tongue are required to be displaced.

The intubation process including the use of the claimed device will generally be performed with the patient is reclining on his/her back. The medical professional initially manipulates the jaw of the patient in well-known fashion for entry of the distal end of oral appliance 10 into the mouth of the patient. During this part of the procedure, balloon 18 will usually be in a deflated configuration. The distal end of device 10 is then advanced into the mouth of the patient and positioned at the back of the mouth in the region of the epiglottis.

The user then inflates balloon 18 via balloon inflation tube 22. Inflation of balloon 18 gently moves the tongue and soft palate out of the way and lifts the epiglottis resulting in the user gaining access to the vocal cords. The user then positions the distal end of an endotracheal tube at the proximal end 14 of elongated member 12. The endotracheal tube is advanced along upper surface 20 of elongated member 12 and into the mouth of the patient. The endotracheal tube is further advanced through lumen 24 of balloon 18, past the vocal cords and into the trachea.

Figure 6:
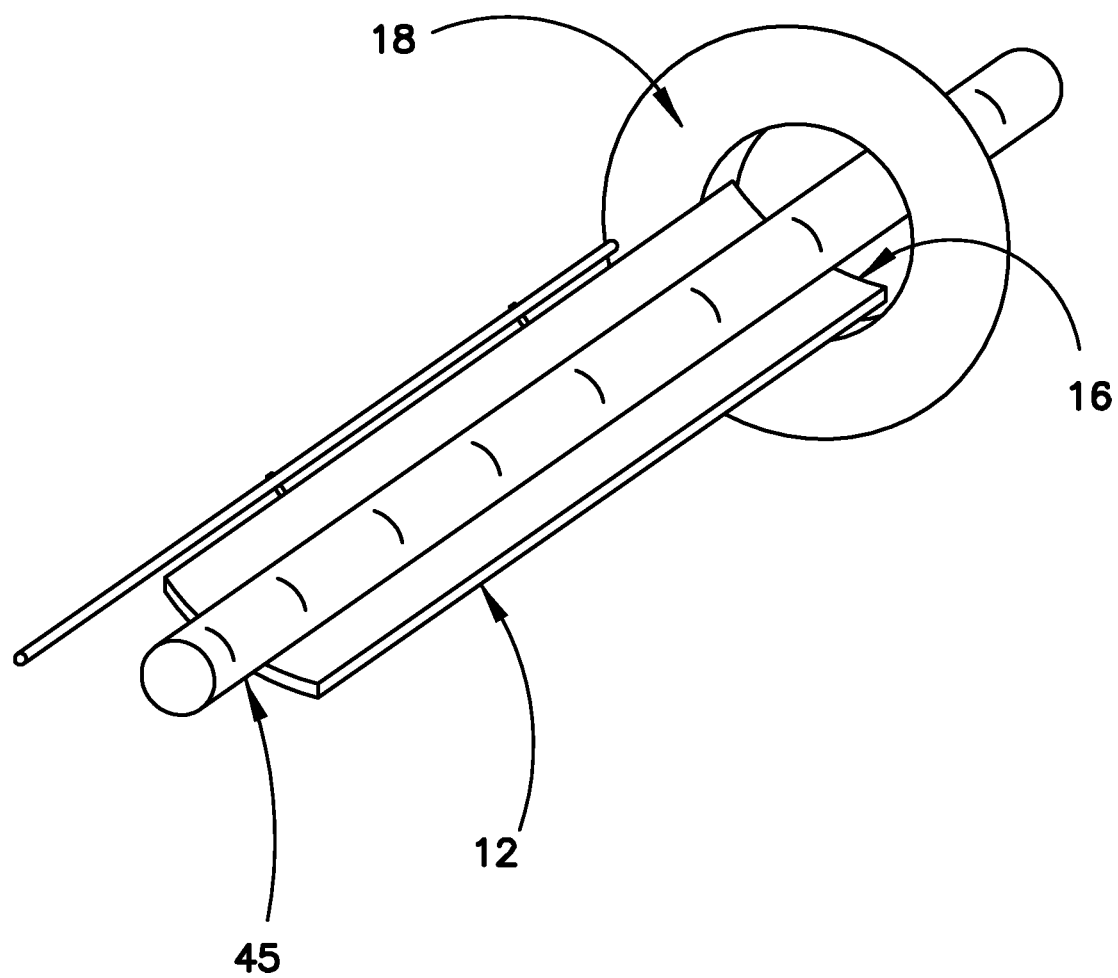
FIG. 6 is an illustration of an oral appliance according to one embodiment of the present invention illustrating the positioning of an intubation tube on the device.

FIG. 6 illustrates intubation tube 45 positioned on elongated element 12 and extending through the lumen of balloon 18, which is shown in an inflated configuration. In this figure, the distal end 16 of elongated element 12 extends through the lumen of balloon 18 to help facilitate placement of the tube.

After placement of the endotracheal tube, oral appliance 10 may be removed from the mouth of the patient. For example, balloon 18 may be deflated and the distal end of oral appliance 10 moved towards the front of the mouth and out of the mouth.

The use of the oral appliance as disclosed above allows for the intubation of a patient without the use of a laryngoscope or video laryngoscope and can offer significant advantages compared with the use of. The device can be used on all patients but will be particularly helpful for patients with Malenpatti Score of 2-4. In addition, the device can be used to intubate a patient with c-spine injury because the use will not need to manipulate the neck.

Another aspect of the present invention provides a kit including the oral appliance as disclosed above. In certain embodiments the kit also includes at least one of an intubation tube, a syringe, pump or other device for inflation the balloon and an inflation medium. The inflation medium may be, for example, air or saline. The components of the kit may be packaged in a sterilized condition. In other embodiments, the oral appliance as disclosed above may be a single use device or may be reusable.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. An oral appliance for exposing vocal cords in a patient's mouth during an intubation procedure, comprising
   a single elongated member extending longitudinally from a proximal end to a distal end, wherein the proximal end of the elongated member forms a proximal end of the oral appliance,
   the elongated member having a concave upper surface extending laterally between a first edge and a second edge, the elongated member ending at the first and second edges along the entire length of the elongated member between the proximal and distal ends, the elongated member forming a channel extending from the proximal end to the distal end, wherein the channel extends from the first edge along the concave upper surface and ends at the second edge and wherein the channel is open above the first and second edges between the proximal end and the distal end, wherein the concave upper surface of the elongated member is adapted to face towards an upper portion of the mouth of a patient when the oral appliance is positioned within the patient, and a single inflatable balloon, wherein the single inflatable balloon attaches the elongated member near the distal end, the inflatable balloon having a central lumen when inflated, wherein the central lumen extends upwards beyond the first edge and the second edge when inflated, wherein the central lumen aligns with the channel to form a continuous pathway from the proximal end to a distal end of the oral appliance and wherein the concave upper surface is open from the proximal end of the elongated member to a proximal end of the inflatable balloon to allow placement of an intubation tube onto the concave upper surface from above when the device is positioned in the mouth of the patient.

2. The oral appliance of claim 1, wherein the inflatable balloon assumes a ring shape around the central lumen when in an inflated configuration, and wherein the central lumen aligns with the channel in the concave upper surface of the elongated member to form the continuous pathway from the proximal end to the distal end of the oral appliance.

3. The oral appliance of claim 1, wherein the inflatable balloon comprises a first end, a central region and a second end, wherein the central region attaches to the elongated member and wherein the first and second ends extend up from the concave upper surface of the elongated member and around the central lumen to form the continuous pathway from the proximal end to the distal end of the oral appliance.

4. The oral appliance of claim 1, wherein the inflatable balloon comprises a central region, a first end and a second end, wherein the first and second ends attach to the elongated member and wherein the central region extends above an upper surface of the elongated member and around the central lumen to form the continuous pathway from the proximal end to the distal end of the oral appliance.

5. The oral appliance of claim 1, wherein the inflatable balloon is a toroidal balloon.

6. The oral appliance of claim 1, further comprising an inflation tube extending from the proximal end to the inflatable balloon and in fluid communication with the inside of the inflatable balloon.

7. The oral appliance of claim 6, further comprising a valve positioned in the inflation tube.

8. The oral appliance of claim 1, wherein the inflatable balloon assumes a lateral dimension of between 1 inch and 3 inches when inflated.

9. The oral appliance of claim 1, wherein the elongated member is a laterally curved member having a longitudinal dimension of between 2 inches and 6 inches.

10. The oral appliance of claim 1, wherein the elongated member comprises a biocompatible polymer.

11. The oral appliance of claim 10, wherein the polymer is selected from the group consisting of polyethylene, a polyurethane, polyvinyl chloride and silicone.

12. The oral appliance of claim 1, wherein the inflatable balloon is a compliant inflatable balloon and comprises a material selected from the group consisting of silicone, polyurethane and nylon elastomer.

13. The oral appliance of claim 1, wherein the inflatable balloon in a semi-compliant inflatable balloon and comprises a material selected from the group consisting of polyethylene terephthalate, nylon and polyurethane.

14. A kit comprising:
the oral appliance of claim 1, and
at least one of a balloon inflation device and an intubation tube;
wherein the oral appliance, and the at least one of the balloon inflation device and the intubation tube are supplied packaged in a sterile condition.

15. The oral appliance of claim 1, wherein the elongated member extends through the lumen and wherein the inflatable balloon attaches to a lower surface of the elongated member.

16. A method for intubating a patient, the method comprising:
inserting a distal end of an oral appliance into a mouth of the patient, wherein the oral appliance comprises:
a single elongated member extending longitudinally from a proximal end to a distal end, wherein the proximal end of the elongated member forms a proximal end of the oral appliance, the elongated member having a concave upper surface extending laterally between a first edge and a second edge, the elongated member ending at the first and second edges along the entire length of the elongated member between the proximal and distal ends, the elongated member forming a channel extending from the proximal end to the distal end, wherein the channel extends from the first edge along the concave upper surface and ends at the second edge and wherein the channel is open above the first and second edges between the proximal end and the distal end, and
a single inflatable balloon, wherein the single inflatable balloon attaches to the elongated member near the distal end, the inflatable balloon having a central lumen when inflated; wherein the central lumen aligns with the channel to form a continuous pathway from the proximal end to a distal end of the oral appliance, wherein the central lumen extends upwards beyond the first edge and the second edge and wherein the concave upper surface is open from the proximal end of the elongated member to a proximal end of the inflatable balloon to allow placement of an intubation tube onto the concave upper surface from above when the device is positioned in the mouth of the patient;
positioning the inflatable balloon at the back of the mouth of the patient, in the region of the epiglottis, with the concave upper surface facing towards an upper portion of the mouth of the patient;
inflating the inflatable balloon to a degree sufficient to lift the epiglottis and to expose vocal cords of the patient;
positioning an intubation tube on the concave upper surface; and
advancing the intubation tube distally through the central lumen, whereby a distal end of the intubation tube is positioned in the trachea of the patient.

17. The method of claim 16, wherein the inflatable balloon is selected from the group consisting of a ring-shaped balloon, a toroidal balloon, and a curved elongated balloon.

18. The method of claim 16, wherein the inflatable balloon is a toroidal balloon.

19. The method of claim 16, wherein the inflatable balloon is a compliant inflatable balloon and comprises a material selected from the group consisting of silicone, polyurethane and nylon elastomer.

20. The method of claim 16, further comprising:
- deflating the inflatable balloon after positioning the intubation tube; and
- removing the oral appliance from the mouth of the patient while maintaining the intubation tube in place.

* * * * *